(12) United States Patent
Esses

(10) Patent No.: US 10,398,798 B2
(45) Date of Patent: Sep. 3, 2019

(54) AIR FRESHENER WITH FAN

(71) Applicant: Alfred Esses, Brooklyn, NY (US)

(72) Inventor: Alfred Esses, Brooklyn, NY (US)

(73) Assignee: Alfred Esses, Brooklyn, NY (US)

( * ) Notice: Subject to any disclaimer, the term of this patent is extended or adjusted under 35 U.S.C. 154(b) by 154 days.

(21) Appl. No.: 14/988,134

(22) Filed: Jan. 5, 2016

(65) Prior Publication Data
US 2017/0189572 A1   Jul. 6, 2017

(51) Int. Cl.
| | |
|---|---|
| *A61L 9/04* | (2006.01) |
| *A61L 9/12* | (2006.01) |
| *F04D 1/00* | (2006.01) |
| *F04D 25/08* | (2006.01) |

(52) U.S. Cl.
CPC ............ *A61L 9/122* (2013.01); *A61L 9/04* (2013.01)

(58) Field of Classification Search
CPC .................................................. A61L 9/122
USPC ............................................................ 422/5
See application file for complete search history.

(56) References Cited

U.S. PATENT DOCUMENTS

| | | | | |
|---|---|---|---|---|
| 5,932,147 | A * | 8/1999 | Chen ................... | A61L 9/122 239/56 |
| 6,102,660 | A * | 8/2000 | Lee ..................... | A61L 9/122 416/146 R |
| 2003/0231958 | A1* | 12/2003 | Murray, Jr. ........ | F04D 19/002 416/146 R |
| 2005/0084413 | A1* | 4/2005 | Stanley, III ........ | A41G 1/006 422/5 |
| 2009/0123345 | A1* | 5/2009 | Yang .................. | A61L 9/122 422/124 |
| 2012/0321492 | A1* | 12/2012 | Zhu .................... | F04D 25/08 417/410.1 |

* cited by examiner

Primary Examiner — Kevin Joyner
Assistant Examiner — Holly M Mull
(74) Attorney, Agent, or Firm — Moritt Hock & Hamroff LLP; Bret P. Shapiro

(57) ABSTRACT

Technologies are generally described for devices and methods effective to disperse fragrance from a material. A first portion of a housing of an air freshener device may be detached from a second portion of the housing. A ring-shaped scented material may be installed into an enclosure formed between the first portion of the housing and the second portion of the housing. The first portion of the housing may be fastened to the second portion of the housing. A fan may be powered to cause the fan to rotate around an axis. A fragrance of the scented material may be dispersed with air blown from the fan. The first portion and the second portion of the housing may be centered around the axis when the first portion of the housing is fastened to the second portion of the housing.

9 Claims, 3 Drawing Sheets

AIR FRESHENER WITH FAN

BACKGROUND

Air fresheners reduce or mask undesired odors and emit pleasant odors. Air fresheners typically emit a pleasant odor in the form of a fragrance. Air fresheners include sprays, candles, oils, gels, and plug-ins.

SUMMARY OF THE INVENTION

In one example, devices are generally described. The devices may have a first end and a second end distal from the first end. The devices may comprise a fan component disposed at the first end of the device. The devices may comprise a first housing coupled to the fan component. The devices may comprise a motor. The motor may be effective to rotate the fan component. The motor may be enclosed within the first housing. The devices may comprise a second housing. The second housing may include a first side facing the first end of the device. The second housing may include a second side facing the second end of the device. The first side may be formed so as to include a first vent. The second side may be formed so as to include a second vent. The second housing may surround at least a portion of the first housing. The devices may comprise a flexible arm. The flexible arm may include a conductor. The flexible arm may have a first end and a second end distal from the first end. The first end of the flexible arm may be connected to the first housing. The devices may comprise a connector disposed at the second end of the device. The connector may be coupled to the second end of the flexible arm. The connector may be electrically coupled to the motor through the conductor of the flexible arm. The connector may be effective to couple to a power source in order to provide electric current to the motor. The fan component may be effective to rotate around an axis. The first housing and the second housing may be centered around the axis. The first end of the flexible arm may be centered around the axis. The first vent and the second vent may be oriented such that at least some air pulled by the fan component flows through the first vent and the second vent in an arcuate direction relative to the axis.

In another example, methods of disbursing scent from an air freshener device having a first end and a second end distal from the first end, are described. The methods may comprise detaching a first portion of a housing from a second portion of the housing. The first portion of the housing may include a first side facing the first end of the air freshener device. The second portion of the housing may include a second side facing the second end of the air freshener device. The first side may be formed so as to include a first vent. The second side may be formed so as to include a second vent. The methods may comprise installing a ring shaped scented material into an enclosure formed between the first portion of the housing and the second portion of the housing. The methods may comprise fastening the first portion of the housing to the second portion of the housing. The methods may comprise powering a fan to cause the fan to rotate around an axis. The fan may be coupled to the second portion of the housing so that, by the rotation of the fan, a fragrance of the scented material is disbursed with air blown from the fan. The first portion and the second portion of the housing may be centered around the axis when the first portion of the housing is fastened to the second portion of the housing. The first vent and the second vent may be oriented such that at least some air pulled by the fan flows through the first vent and the second vent in an arcuate direction relative to the axis.

In another example, devices are generally described. The devices may have a first end and a second end distal from the first end. The devices may comprise a fan component disposed at the first end of the device. The devices may comprise a first housing coupled to the fan component. The devices may comprise a motor. The motor may be effective to rotate the fan component. The motor may be enclosed within the first housing. The devices may comprise a second housing. The second housing may include a first side facing the first end of the device. The second housing may include a second side facing the second end of the device. The first side of the second housing may be formed so as to include a first vent. The second side of the second housing may be formed so as to include a second vent. The second housing may surround at least a portion of the first housing. The devices may comprise a ring shaped scented material installed within an enclosure formed by the second housing. The ring shaped scented material may include at least one permeable membrane effective to allow scented particles to mix with air surrounding the ring shaped scented material. The devices may comprise a flexible arm. The flexible arm may include a conductor. The flexible arm may have a first end and a second end distal from the first end. The first end of the flexible arm may be connected to the first housing. The devices may comprise a connector disposed at the second end of the device. The connector may be coupled to the second end of the flexible arm. The connector may be electrically coupled to the motor through the conductor of the flexible arm. The connector may be effective to couple to a power supply in order to provide electric current to the motor. The fan component may be effective to rotate around an axis. The first housing and the second housing may be centered around the axis. The first end of the flexible arm may be centered around the axis.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

Figure 1:
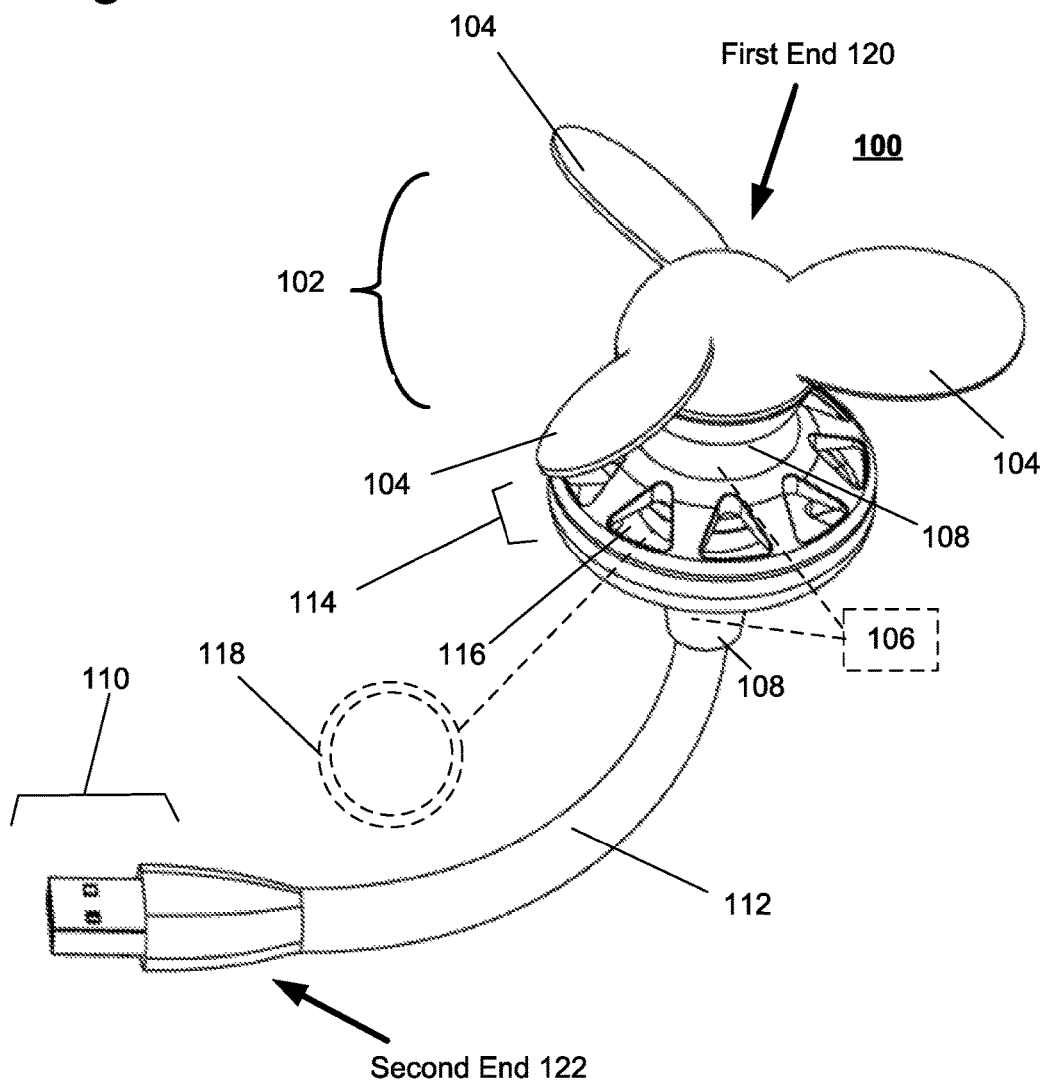
FIG. 1 is an isometric view of an air freshener with fan.

all in accordance with an embodiment of the invention.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

FIG. 1 is an isometric view of an air freshener with fan 100. Air freshener with fan 100 may include a fan component 102. Fan component 102 may include blades 104. Blades 104 may be effective to blow or otherwise displace air when fan component 102 is rotated. Although three blades 104 are depicted in FIG. 1, a greater or lesser number of blades 104 may be used. In some examples, fan component 102 may be rotated by a motor 106. Motor 106 may be enclosed within a housing 108 of air freshener with fan 100. Motor 106 may be any type of electric motor and may be effective to rotate fan component 102 around an axis. In some examples, motor 106 may rotate an axel which may, in turn, rotate fan component 102. In various examples, air freshener with fan 100 may include a selectable switch which may be effective to control operation of motor 106 at different speeds. For example, a selectable switch may be positioned on housing 108 and may allow a user of air freshener with fan 100 to select between low, medium, and high speeds of operation of motor 106. In various other examples, a selectable switch may control the direction in which motor 106 rotates fan component 102 (e.g., clockwise or counterclockwise). In some examples, the selectable switch which controls the speed of operation of motor 106 may be the same switch which controls the direction in which motor 106 rotates fan component 102. In other examples, the selectable switch which controls the speed of operation of motor 106 may be different from the switch which controls the direction in which motor 106 rotates fan component 102.

In some examples, housing 108 may be sized and shaped so as to form one or more enclosures. As depicted, in various examples, housing 108 may be located under fan component 102 when fan component 102 is the top most portion of air freshener with fan 100. In some examples, housing 108 may be coupled to fan component 102. Motor 106 may be enclosed within an enclosure of housing 108. Motor 106 may be electrically coupled to connector 110. In various examples, connector 110 may be a universal serial bus ("USB") connection, a 12 volt "car charger" connector, a pronged wall outlet connector (such as a connector for a 120 volt alternating current home electrical outlet), or any other connection type effective to couple to a power source and provide electrical current to motor 106. In various examples, fan component 102 may be disposed at a first end 120 of air freshener with fan 100 and connector 110 may be disposed at a second end 122 of air freshener with fan 100. Second end 122 of air freshener with fan 100 may be distal to first end 120 of air freshener with fan 100.

In some examples, air freshener with fan 100 may include a flexible arm 112. In various examples, flexible arm 112 may be connected to housing 108 and/or to connector 110. Flexible arm 112 may be flexible so that a user may position fan component 102 with respect to connector 110, when connector 110 is coupled to a power source. In various examples, a user may position flexible arm 112 such that air displaced by fan component 102 is blown towards the user. In various examples, flexible arm 112 may be flexible along its length. Upon being flexed or bent into a desired position, flexible arm 112 may remain in the desired position.

In some examples, an outer surface of flexible arm 112 may be formed from an insulating material. In various examples, flexible arm 112 may include wires, fibers, or other conductive materials to electrically couple connector 110 to motor 106. In some examples, conductive materials of flexible arm 112 may be formed on an interior of flexible arm 112 to so that the conductive materials are surrounded by insulating material. In various examples, one end of flexible arm 112 may be coupled to housing 108 while the other end of flexible arm 112 may be coupled to connector 110. In some examples, the end of flexible arm 112 that is connected to housing 108 may be centered around an axis of rotation of fan component 102.

Air freshener with fan 100 may include an air freshener housing 114. As will be discussed in further detail below, air freshener housing 114 may include a first side facing towards fan component 102 and a second side facing away from fan component 102. The first side and the second side of air freshener housing 114 may be formed so as to include one or more vents 116. In some examples, at least a portion of air freshener housing 114 may be coupled to fan component 102. In some other examples, air freshener housing 114 may be formed around housing 108 such that air freshener housing 114 surrounds at least a portion of housing 108. In various examples, air freshener housing 114 may be formed from a translucent material. Air freshener housing 114 may be sized and shaped so as to form an enclosure into which a scented material 118 may be installed, placed, or fit. In some examples, scented material 118 may be a liquid, oil, gel, aerosol, or solid material (such as ceramic, paper, etc.) infused with a fragrance. In some other examples, scented material 118 may include scented oil encapsulated by a plastic ring or disc. The plastic ring or disc may include a permeable membranous portion effective to allow scented particles to escape the ring or disc. The scented oil may evaporate, allowing scented particles to mix with the air surrounding the scented material to created scented air. In some examples, heating scented material 118 may accelerate the evaporation of scented material 118. In some examples, resistive heating elements may be installed within housing 108. The resistive heating elements may be effective to heat scented material 118. In other examples, heat produced from the operation of motor 106 may be effective to heat scented material 118. In various other examples, air flowing over scented material 118 may accelerate evaporation of scented material 118. For example, fan component 102 may cause air to flow over scented material 118 when motor 106 is rotating fan component 102. Fragrances may be any desirable fragrance, including fruit scents, pine scents, perfumes, new car smell, etc. The operation of fan component 102 may help to disburse fragrance into the spaces proximate to air freshener with fan 100 by disbursing fragrance mixed with air blown from fan component 102.

Figure 2:
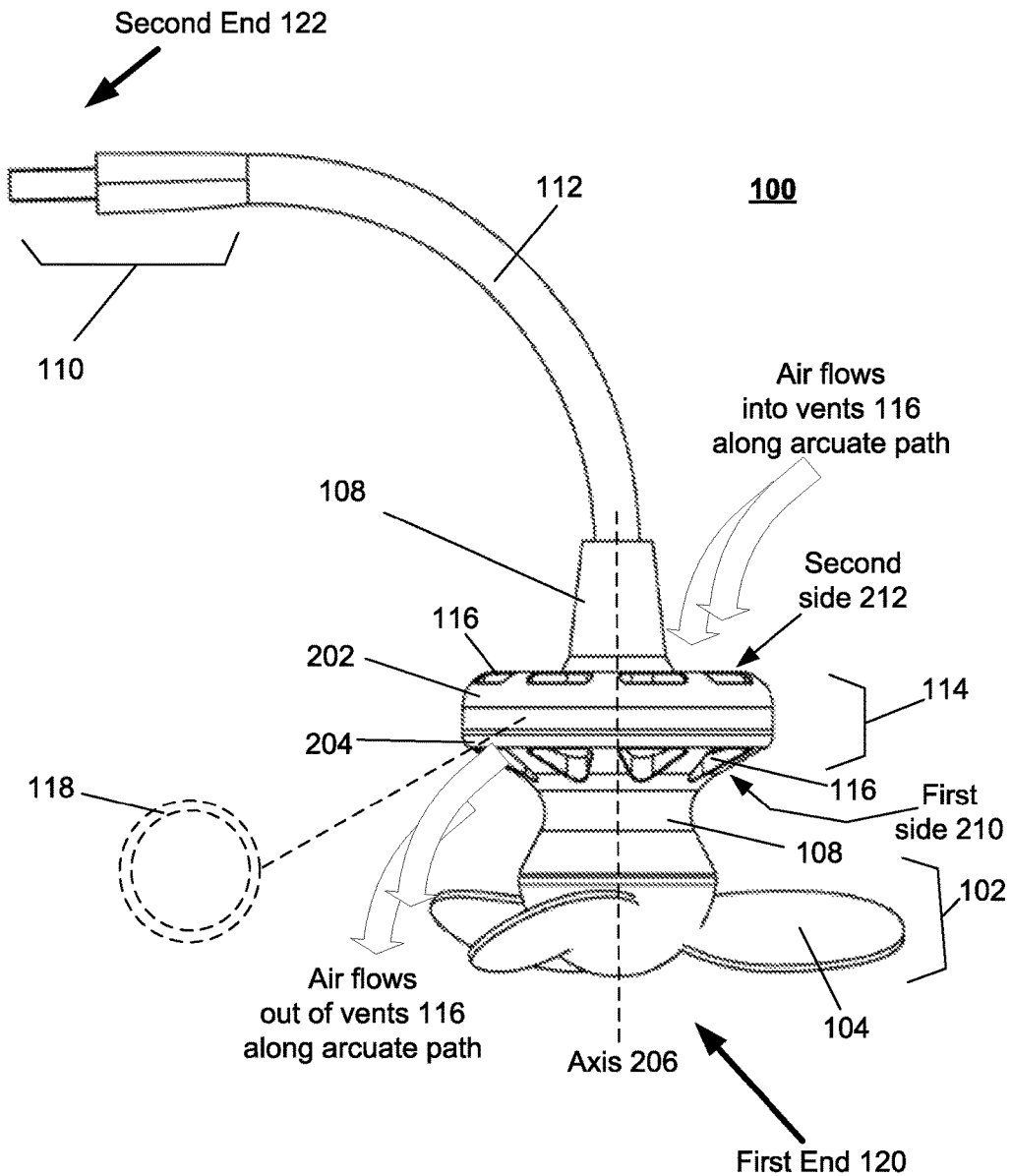
FIG. 2 is a side view of an air freshener with fan.

FIG. 2 depicts a side view of an air freshener with fan 100. Those components illustrated in FIG. 2 which are identical to components of FIG. 1 will not be described again herein for purposes of clarity and brevity. Fan component 102 may be configured to rotate around an axis 206. Housing 108 and air freshener housing 114 may be centered around axis 206. Air freshener housing 114 may include an upper portion 204 (e.g., the side of air freshener housing 114 proximate to fan component 102 and first end 120) and a lower portion 202 (e.g., the side of air freshener housing 114 proximate to flexible arm 112 and second end 122). Upper portion 204 and/or lower portion 202 may be formed in such a way that upper portion 204 and/or lower portion 202 include vents 116 on a first side 210 and a second side 212 of air freshener housing 114. First side 210 of air freshener housing 114 may face first end 120 of air freshener with fan 100. Second side 212 of air freshener housing 114 may face second end 122 of air freshener with fan 100. In various examples, vents 116 may be oriented such that at least some air pulled by fan component 102 may flow through air freshener housing 114 in an arcuate direction relative to axis 206. In some examples, air blown into and/or out of air freshener housing 114 may be scented by scented material 118 when scented material 118 is installed within air freshener housing 114.

In various examples, lower portion 202 may be coupled to upper portion 204 using a fastener, such as screw-threads, snaps, clasps, or various other fasteners. In some examples, lower portion 202 may be decoupled from upper portion 204 by unscrewing, unsnapping, or otherwise unfastening lower portion 202 from upper portion 204. As will be described in further detail below, lower portion 202 may be detachable from upper portion 204 in order to remove and/or install scented material 118 into and/or out of air freshener housing 114. Similarly, lower portion 202 may be fastened to upper portion 204 by screw-threads, snaps, clasps, or various other fasteners.

Figure 3:
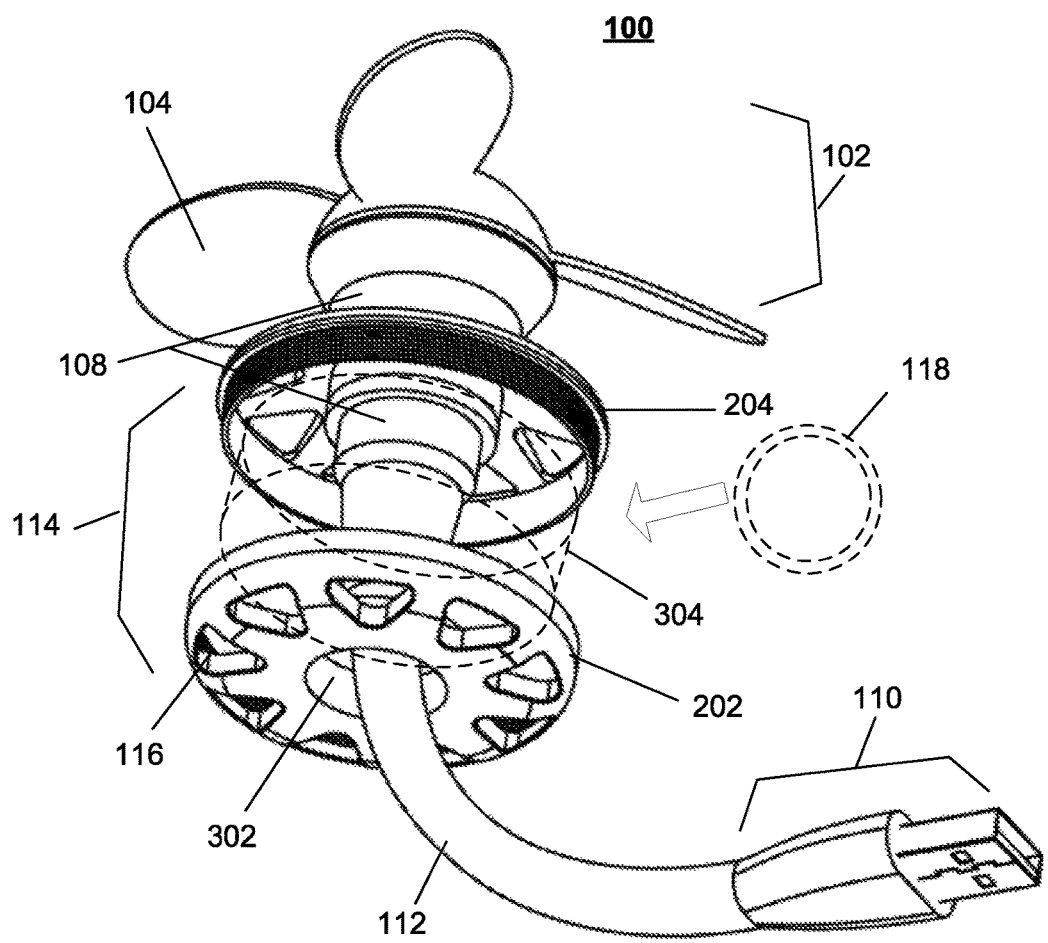
FIG. 3 is an isometric view of an air freshener with fan depicting a detachable portion.

FIG. 3 depicts an isometric view of air freshener with fan 100 including a detachable lower portion 202. Those components illustrated in FIG. 3 which are identical to components of FIGS. 1 and 2 will not be described again herein for the purposes of clarity and brevity.

In some examples, lower portion 202 may be detachable from upper portion 204. In various examples, lower portion 202 may be detached from upper portion 204 in order to remove and/or install scented material 118 within an enclosure 304. Enclosure 304 may be formed by upper portion 204 and lower portion 202 of air freshener housing 114. In various examples, lower portion 202 may be sized and shaped so as to include an opening 302. Lower portion 202 may be formed such that connector 110 and flexible arm 112 may be threaded through opening 302. In some examples, lower portion 202 may be removed from air freshener with fan 100 by threading flexible arm 112 through opening 302 of lower portion 202 and allowing connector 110 to pass through opening 302. In various examples, lower portion 202 may be removed from air freshener with fan 100 to remove old scented material 118 and/or install new scented material 118 within enclosure 304 formed by air freshener housing 114. In some examples where scented material 118 is formed in the shape of a ring, connector 110 and flexible arm 112 may be threaded through the open portion of ring-shaped scented material 118 so that ring-shaped scented material 118 may be installed within or removed from enclosure 304. Connector 110 and flexible arm 112 may be likewise threaded through opening 302 of lower portion 202. Lower portion 202 may be coupled to upper portion 204 with scented material 118 situated within enclosure 304.

Among other potential benefits, a device in accordance with the disclosure may provide a desired fragrance to freshen the surrounding air. A fan component of the air freshener may aid in the dispersal of the fragrance from the air freshener and may provide a breeze for a user of the air freshener and fan device. Additionally, the flexible arm may allow a user to position the air freshener and fan device so that air is blown, and scent is dispersed, in a desired direction. The connector of the air freshener and fan device may allow a user to plug the air freshener and fan device into a conveniently located power supply, such as, for example, a universal serial bus port. In some cases, plugging the air freshener and fan device into a power supply may anchor the air freshener and fan device so that the fan component may be positioned by adjusting the flexible arm.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device having a first end and a second end distal from the first end, the device comprising:
   a fan component disposed at the first end of the device, wherein the fan component includes a first side and a second side and the first end of the device terminates at the first side of the fan component;
   a first housing coupled to the fan component, wherein the first housing is coupled to the second side of the fan component and extends away from the fan component;
   a motor, the motor effective to rotate the fan component, wherein the motor is enclosed within the first housing;
   a second housing, wherein the second housing includes a first side facing the first end of the device and a second side facing the second end of the device, wherein the first side is formed so as to include a first vent and the second side is formed so as to include a second vent, wherein the second housing surrounds at least a portion of the first housing;
   a flexible arm, the flexible arm including a conductor and having a first end and a second end distal from the first end, wherein the first end is connected to the first housing; and
   a connector disposed at the second end of the device, the connector coupled to the second end of the flexible arm, wherein the connector is electrically coupled to the motor through the conductor of the flexible arm, and wherein the connector is effective to couple to a power source in order to provide electric current to the motor;
   wherein:
      the fan component is effective to rotate around an axis;
      the first housing and the second housing are centered around the axis;
      the first end of the flexible arm is centered around the axis;
      the first vent and the second vent are oriented such that when the fan component is rotated by the motor, at least some of the air pulled by the fan component is pulled so as to flow through the first vent and the second vent in an arcuate direction relative to the axis.

2. The device of claim 1, wherein the second housing is sized and shaped to fit a ring-shaped scented material within an enclosure formed by the second housing and at least some of the air pulled by the fan component through the first vent and the second vent in an arcuate direction relative to the axis is scented by scented material prior to reaching the fan component.

3. The device of claim 1, wherein the connector is a universal serial bus connector.

4. The device of claim 1, wherein the second housing includes a first portion coupled to a second portion using a fastener.

5. The device of claim 4, wherein the second portion is detachable from the first portion.

6. The device of claim 4, wherein the second portion is sized and shaped so as to include an opening, wherein the opening is large enough for the connector to pass through the opening.

7. The device of claim 1, wherein the flexible arm is flexible along a length of the flexible arm.

8. The device of claim 1, further comprising a scented material located inside an enclosure formed by the second housing;
   wherein the scented material is formed in the shape of a ring, and wherein the scented material is installed in the housing by threading the connector and the flexible arm through the ring.

9. The device of claim 8, wherein the scented material includes a liquid oil, a gel, or a solid, and wherein the scented material is in the shape of a ring.

* * * * *